US012685554B2

(12) United States Patent (10) Patent No.: US 12,685,554 B2

Liu et al. (45) Date of Patent: Jul. 21, 2026

(54) MULTIFUNCTIONAL SURGICAL INSTRUMENT

(71) Applicant: Innolcon Medical Technology (Suzhou) Co., Ltd., Suzhou (CN)

(72) Inventors: Ke Liu, Suzhou (CN); Xiaohe Yuan, Suzhou (CN); Zhenzhong Liu, Suzhou (CN); Zhongyu Yan, Suzhou (CN); Wei Luo, Suzhou (CN)

(73) Assignee: Innolcon Medical Technology (Suzhou) Col., Ltd., Suzhou (CN)

( * ) Notice: Subject to any disclaimer, the term of this patent is extended or adjusted under 35 U.S.C. 154(b) by 360 days.

(21) Appl. No.: 18/547,109

(22) PCT Filed: Apr. 7, 2022

(86) PCT No.: PCT/CN2022/085536

§ 371 (c)(1),
(2) Date: Aug. 18, 2023

(87) PCT Pub. No.: WO2022/242353

PCT Pub. Date: Nov. 24, 2022

(65) Prior Publication Data

US 2025/0268619 A1 Aug. 28, 2025

(30) Foreign Application Priority Data

May 21, 2021 (CN) .......................... 202110556275.3

(51) Int. Cl.
A61B 17/32 (2006.01)
A61B 17/29 (2006.01)

(52) U.S. Cl.
CPC ................. A61B 17/320092 (2013.01); A61B 2017/2923 (2013.01); A61B 2017/320074 (2017.08)

(58) Field of Classification Search
CPC ................ A61B 17/29; A61B 17/2909; A61B 17/320092; A61B 2017/00367;
(Continued)

(56) References Cited

U.S. PATENT DOCUMENTS

| 5,391,144 | A | 2/1995 | Sakurai et al. | |
| 2018/0206906 | A1* | 7/2018 | Moua | A61B 18/1445 |
| 2020/0315685 | A1* | 10/2020 | Brady | A61B 18/1206 |

FOREIGN PATENT DOCUMENTS

| CN | 106264710 A | 1/2017 |
| CN | 106491201 A | 3/2017 |

(Continued)

OTHER PUBLICATIONS

International Search Reporting corresponding to international application PCT/CN2022/085536 mailed Jun. 28, 2022 (8 pages).

*Primary Examiner* — Robert A Lynch

(74) *Attorney, Agent, or Firm* — Armstrong Teasdale LLP

(57) ABSTRACT

Disclosed herein is a multifunctional surgical instrument, including a housing, a trigger provided on the housing, an ultrasonic transducer provided inside the housing, and a blade shaft assembly that transmits ultrasonic energy generated by the ultrasonic transducer and electrical energy generated by the system. The blade shaft assembly includes a waveguide, with a proximal end thereof being fixedly connected to the ultrasonic transducer, and a distal end thereof extending out of the housing and forming an ultrasonic blade. A clamping arm is opened and closed relative to the waveguide under the action of a first driving force. A monopolar sleeve is sleeved on an outer side of the waveguide and is axially movable relative to the housing under the action of a second driving force.

24 Claims, 10 Drawing Sheets

(58) Field of Classification Search
CPC .... A61B 2017/2923; A61B 2017/2926; A61B
2017/2932; A61B 2017/2939; A61B
2017/320074; A61B 18/1445; A61B
2018/0019; A61B 2018/00196; A61B
2018/00607; A61B 2018/00958; A61B
2018/00994; A61B 2018/1253; A61B
2018/1452
See application file for complete search history.

(56) References Cited

FOREIGN PATENT DOCUMENTS

| | | | |
|---|---|---|---|
| CN | 107260258 | A | 10/2017 |
| CN | 206979572 | U | 2/2018 |
| CN | 108348271 | A | 7/2018 |
| CN | 108888336 | A | 11/2018 |
| CN | 109414285 | A | 3/2019 |
| CN | 111110344 | A | 5/2020 |
| CN | 111658128 | A | 9/2020 |
| CN | 113229891 | A | 8/2021 |

* cited by examiner (a)

(b)

(c)

(d)

MULTIFUNCTIONAL SURGICAL INSTRUMENT

CROSS-REFERENCE TO RELATED APPLICATIONS

This application is a U.S. National Phase Application of International Patent Application No. PCT/CN22/85536, filed Apr. 7, 2022, which claims priority to Chinese Patent Application No. 202110556275.3, filed May 21, 2021, each of which is hereby incorporated by reference herein.

FIELD OF THE PRESENT DISCLOSURE

The present invention relates to the field of medical instruments, in particular to a multifunctional surgical instrument that combines ultrasonic energy and high-frequency energy.

BACKGROUND OF THE PRESENT DISCLOSURE

The ultrasonic surgical scalpel (herein ultrasound scalpel in short) refers to a instrument which further amplifies the ultrasonic vibration obtained by a piezoelectric transducer (the electric energy is transmitted to the piezoelectric transducer by an energy generator, and the electric energy is converted into ultrasonic mechanical energy by the piezoelectric transducer), and uses the amplified ultrasonic vibration through the blade of the surgical scalpel to cut and coagulate soft tissue. The specific structure s disclosed in Chinese patent applications CN201922284962.5, CN201910266779.4 and CN201720533712.9, and generally comprises a housing, a trigger, a blade shaft assembly, and an ultrasonic transducer. A main unit of an ultrasonic surgical system outputs the electric energy required by the ultrasonic scalpel to generate resonance, and the ultrasonic transducer converts the electric energy into mechanical energy which vibrates at ultrasonic frequency and transmits the same to a blade's tip of the ultrasonic scalpel. After the tissue is in contact with the blade's tip, the blade shaft assembly absorbs the ultrasonic energy, the protein hydrogen bond is broken to generate cavitation effect, and then the tissue is coagulated and denatured and to achieve the effect of cutting and coagulation via cutting under the clamping pressure. The ultrasonic surgical scalpel is suitable for fine dissection, and a closure/cutting high-frequency electrotome for electrosurgery is required when closure of large vessels is involved.

The electrotome generally include monopolar or bipolar high-frequency electrosurgical instrument. The monopole electrosurgical instrument has the functions of pure cutting, mixed cutting, monopolar electrocoagulation and electrocautery, while the bipolar electrosurgical instrument mainly has the function of electrocoagulation. The monopolar electrosurgical instrument has an electrical circuit of system—monopole—patient—negative electrode plate—system. The bipolar electrosurgical instrument has an electrical circuit of system—first electrode forcep—tissue to be cut—second electrode forcep—system. Therefore, the monopolar electrosurgical instrument uses a complete electrical circuit to cut and coagulate tissue, which consists of a high-frequency generator within the high-frequency electrotome, a patient polar plate, a connecting wire, and electrodes. In most applications, current is passed through the patient via the effective leads and electrodes, and returned to the generator of the high-frequency electrotome from the patient polar plate and wires thereof, as disclosed in Chinese patents CN 211704821U, CN 209186939U, etc.

The bipolar electrocoagulation is intended to provide high-frequency electric energy to body tissues through the two tips of bipolar forceps to dehydrate and coagulate the blood vessels between the two tips of the bipolar forceps to achieve the purpose of hemostasis. The action range of it is only limited between the two tips of the forceps, and its damage degree and influence range on body tissues are much smaller than that of monopolar mode, which is applicable to the closure of small vessels (diameter <4 mm) and fallopian tube. Therefore, bipolar electrocoagulation is used in more delicate operations, such as cerebral surgery, microsurgery, ENT surgery, obstetrical and gynecological surgery, and hand surgery.

Therefore, in the surgery, a doctor may use a high-frequency electrotome to perform some special operations at the interval of using the ultrasonic surgical scalpel, which results in frequent replacement of the scalpel in actual surgery. Chinese patent CN 209564199U proposes a surgical electrode forceps with high-frequency ultrasonic function. This structure provides the function of ultrasonic surgical scalpel combined with a bipolar electrosurgical instrument, focusing on the improved coagulation function of the bipolar electrosurgical instrument. However, this kind of surgical electrode forceps is too simple in structure and has no corresponding interlocking structure, which is not suitable for fine surgical cutting and even less suitable for minimally invasive laparoscopic surgery.

SUMMARY OF THE PRESENT DISCLOSURE

In order to solve the above-mentioned problems of the prior art, the present invention provides a multifunctional surgical instrument integrating with ultrasonic energy and high-frequency energy.

In order to solve the above technical problem, the present invention provides the following solutions:

A multifunctional surgical instrument, comprising a housing, a trigger provided on the housing, an ultrasonic transducer provided inside the housing, and a blade shaft assembly that transmits ultrasonic energy generated by the ultrasonic transducer and electrical energy generated by the system, wherein the blade shaft assembly comprises:

a waveguide, with a proximal end thereof being fixedly connected to the ultrasonic transducer, and a distal end thereof extending out of the housing and forming an ultrasonic blade;

a connecting sleeve sleeved on the circumference of the waveguide and axially movable with respect to the waveguide;

a support sleeve sleeved on the circumference of the connecting sleeve and axially fixed with respect to the waveguide;

a clamping arm fitted at the distal ends of the connecting sleeve and the support sleeve, and the axial movement of the connecting sleeve drives the clamping arm to open and close relative to the waveguide;

a monopolar sleeve sleeved on the circumference of the support sleeve;

a gearbox provided within the housing, configured to be located at a proximal end of the monopolar sleeve, and drive the monopolar sleeve to move axially relative to the housing; and a sleeve holder axially fixed in the housing, wherein the waveguide and the support sleeve are axially fixed to the sleeve holder and are able to rotate axially at the same time.

Preferably, the sleeve holder, the waveguide and the support sleeve comprises corresponding pin holes respectively, and the three parts are axially fixed by a penetrating pin, and the connecting sleeve is provided with an elongated slot, and the pin penetrates the elongated slot so that the connecting sleeve moves axially relative to the waveguide.

Preferably, the proximal end of the monopolar sleeve has an elongated slot through which the pin penetrates to limit the stroke of the monopolar sleeve.

Preferably, the monopolar sleeve has a circular ring at a proximal end, and a recessed structure is provided at a distal end of a rack coupled to the gearbox, the circular ring being coupled to the recessed structure so that the monopolar sleeve performs a reciprocating move when the rack receives output of the gearbox.

Preferably, the gearbox comprises:

a reciprocating rotary drive gear, a transmission gear set, including a connecting gear and a ratchet, wherein the connecting gear is configured to engage the drive gear and enlarge a transmission distance to the ratchet; the ratchet has a gear meshing with the connecting gear and two claws provided symmetrically on the circumference of the ratchet, a reversing idler wheel, having a single tooth cooperating with the claw, two protrusions symmetrically provided on the circumference of the reversing idler wheel and cooperating with a limiting mechanism of the housing, and an eccentric cylinder axially provided on one end face of the reversing idler wheel, and a rack slider, reciprocatingly and slidably provided in the gearbox and having an elongated slot provided perpendicular to the reciprocating sliding direction, and a short rack provided in correspondence with the reciprocating sliding direction.

Preferably, the short rack enlarges the transmission distance to the rack by means of a conversion gear.

Preferably, the distal end of the connecting sleeve is provided with a square hole, the distal end of the support sleeve is provided with a round hole, a round hole on the clamping arm and the round hole on the distal end of the support sleeve are articulated via a rotating shaft, and a protrusion on the clamping arm is snapped into the square hole on the distal end of the connecting sleeve.

Preferably, the trigger generates a first driving force to drive the connecting sleeve to move axially relative to the waveguide via a horizontal yoke; a circular ring at the proximal end of the connecting sleeve is connected to an annular groove of the horizontal yoke; and the connecting sleeve slides relative to the support sleeve under the pull of the horizontal yoke, and drives the protrusion of the clamping arm to rotate around the rotating shaft to achieve the opening and closing of the clamping arm.

Preferably, the horizontal yoke comprises a distal plastic piece and a proximal metal piece which are connected to each other, wherein the proximal metal piece successively penetrates the first spring and the slider and then pre-compresses the first spring and then is connected to the distal plastic piece; the slider is articulated to the trigger, the distal plastic piece is provided with an annular groove, and further comprises a second spring, wherein the second spring is pre-compressed and mounted between a boss on the proximal metal piece and the housing for providing a restoring force to the horizontal yoke.

Preferably, the bladeshaft assembly further comprises an outer insulation tube and an outer insulation jacket, wherein the outer insulation tube is coated on the outside of the monopolar sleeve and the two are not fixed to each other, the proximal end of the outer insulation tube is connected to a rotating wheel on the housing and rotates with the rotating wheel, and the outer insulation jacket is coated on a distal end of the monopolar sleeve and is fixed with the monopolar sleeve and moves therewith.

Preferably, a first trigger switch and a second trigger switch are provided on the trigger, and a simultaneous trigger preventing structure is provided there between.

The present invention also discloses another multifunctional surgical instrument comprising a housing, a trigger provided on the housing, an ultrasonic transducer provided inside the housing, and a blade shaft assembly that transmits ultrasonic energy generated by the ultrasonic transducer and electrical energy generated by the system, wherein the blade shaft assembly comprises:

a waveguide, with a proximal end thereof being fixedly connected to the ultrasonic transducer, and a distal end thereof extending out of the housing and forming an ultrasonic blade;

a clamping arm, opened and closed relative to the waveguide under the action of a first driving force; and a monopolar sleeve, sleeved on an outer side of the waveguide and axially moving relative to the housing under the action of a second driving force.

Preferably, the source of the second driving force is a gearbox provided in the housing and provided at a proximal end of the monopolar sleeve, wherein the monopolar sleeve has a circular ring at a proximal end, and a rack coupled to the gearbox has a recessed structure at a distal end, and the circular ring is connected to the recessed structure so that the monopolar sleeve performs a reciprocating motion when the rack receives the output of the gearbox.

Preferably, the gearbox comprises:

a power source that outputs forward and reverse reciprocating rotary power;

a ratchet for receiving forward and reverse reciprocating rotary power, the ratchet having a double circumference structure, respectively being a gear for receiving the power and two resilient claws symmetrically arranged at 180° on the circumference of the ratchet, the arrangement face of the claws being parallel to the gear in space;

a rack slider reciprocatingly and slidably provided in the gearbox; and a reversing idler wheel for converting the forward and reverse reciprocating rotation power of the ratchet into an axial reciprocating motion of the rack slider.

Preferably, the inside of the reversing idler wheel comprises a single tooth cooperating with the claw.

Preferably, the reversing idler wheel further has an anti-reversing mechanism comprising two protrusions symmetrically arranged at 180° on the circumference of the reversing idler wheel and cooperating with a limiting mechanism of the housing, wherein the protrusions are of a ratchet tooth structure to restrict the reverse rotation of the reversing idler wheel.

Preferably, the reversing idler wheel further comprises an eccentric cylinder provided axially on one end surface thereof, and the rack slider has an elongated slot provided perpendicular to the reciprocating sliding direction, the eccentric cylinder being inserted into the elongated slot.

Preferably, a sleeve holder axially fixed within the housing is further comprised, the waveguide being axially fixed to the sleeve holder and axially rotatable at the same time.

Preferably, the blade shaft assembly further comprises:

a connecting sleeve sleeved on the circumference of the waveguide and axially movable with respect to the waveguide; and a support sleeve sleeved on the circumference of the connecting sleeve and axially fixed on the sleeve holder together with the waveguide;

wherein the clamping arm is fitted at the distal ends of the connecting sleeve and the support sleeve, the trigger generates a first driving force to drive the connecting sleeve to move axially relative to the waveguide via a horizontal yoke; a circular ring at the proximal end of the connecting sleeve is connected to an annular groove of the horizontal yoke; and the connecting sleeve slides relative to the support sleeve under the pull of the horizontal yoke, and drives a protrusion of the clamping arm to rotate around a rotating shaft to achieve the opening and closing of the clamping arm.

The present invention also discloses another multifunctional surgical instrument comprising a housing, a trigger provided on the housing, and a blade shaft assembly configured to selectively receive and transmit ultrasonic energy provided by an ultrasonic transducer through a switching mechanism located within the housing for cutting and hemostasis, or selectively transmit high-frequency electrical energy to achieve the function of a monopole high-frequency electrotome.

Preferably, the ultrasonic transducer is provided within the housing or external to and attached to the blade shaft assembly.

Preferably, the blade shaft assembly comprises:

a waveguide configured to transmit ultrasonic energy generated by the transducer; and a monopolar sleeve movable relative to the waveguide; wherein when the ultrasonic blade of the waveguide is located at the most distal end, ultrasonic energy is generated to perform cutting and hemostasis; and when the monopolar sleeve is located at the most distal end, high-frequency electric energy is transmitted to achieve the function of the monopole high-frequency electrotome.

Preferably, the blade shaft assembly further comprises:

a connecting sleeve sleeved on the circumference of the waveguide and axially movable with respect to the waveguide;

a support sleeve sleeved on the circumference of the connecting sleeve and axially fixed with the waveguide, a clamping arm fitted at the distal ends of the connecting sleeve and the support sleeve, and the axial movement of the connecting sleeve drives the clamping arm to open and close relative to the waveguide; and a sleeve holder axially fixed in the housing, wherein the waveguide and the support sleeve are axially fixed to the sleeve holder and can rotate axially at the same time.

Preferably, the blade shaft assembly further comprises an outer insulation tube and an outer insulation jacket, wherein the outer insulation tube is coated on the outside of the monopolar sleeve and the two are not fixed to each other, a proximal end of the outer insulation tube is connected to a rotating wheel on the housing and rotates with the rotating wheel, and the outer insulation jacket is coated on a distal end of the monopolar sleeve and is fixed with the monopolar sleeve and moves therewith.

Preferably, the switching mechanism is a gearbox, the monopolar sleeve is driven by the gearbox to move axially relative to the ultrasound guide rod, the gearbox comprising:

a reciprocating rotary drive gear, a transmission gear set, including a connecting gear and a ratchet, the connecting gear is configured to engage the drive gear and enlarge a transmission distance to the ratchet; the ratchet has a gear meshing with the connecting gear and two claws provided symmetrically on the circumference of the ratchet, a reversing idler wheel, having a single tooth cooperating with the claw, two protrusions symmetrically provided on the circumference of the reversing idler wheel and cooperating with a limiting mechanism of a gear seat, and an eccentric cylinder axially provided on one end face of the reversing idler wheel, and a rack slider, reciprocatingly and slidably provided in the gearbox and having an elongated slot provided perpendicular to the reciprocating sliding direction, and a short rack provided in correspondence with the reciprocating sliding direction.

Preferably, a first trigger switch and a second trigger switch are provided on the trigger, and a simultaneous trigger preventing structure is provided there between.

Advantageous effects of the present invention are mainly as follows: A multifunctional surgical instrument combining ultrasonic energy and high-frequency energy is provided, which can achieve the ultrasonic energy cutting and hemostasis function and can also realize the function of monopole high-frequency electrotome. The present invention integrates two functions of a surgical scalpel to simplify the process of frequently changing surgical knives in an operating room, which may facilitate use by a surgeon. The present invention also has a simultaneous trigger preventing structure for effectively prevents simultaneous triggering of the switch.

DESCRIPTION OF THE EMBODIMENTS

The present invention will be described in detail with reference to the embodiments shown in the accompanying drawings. However, these embodiments are not limited to the present invention, and structural, methodological, or functional modifications made by a person skilled in the art according to these embodiments are included in the scope of the present invention.

Figure 1:
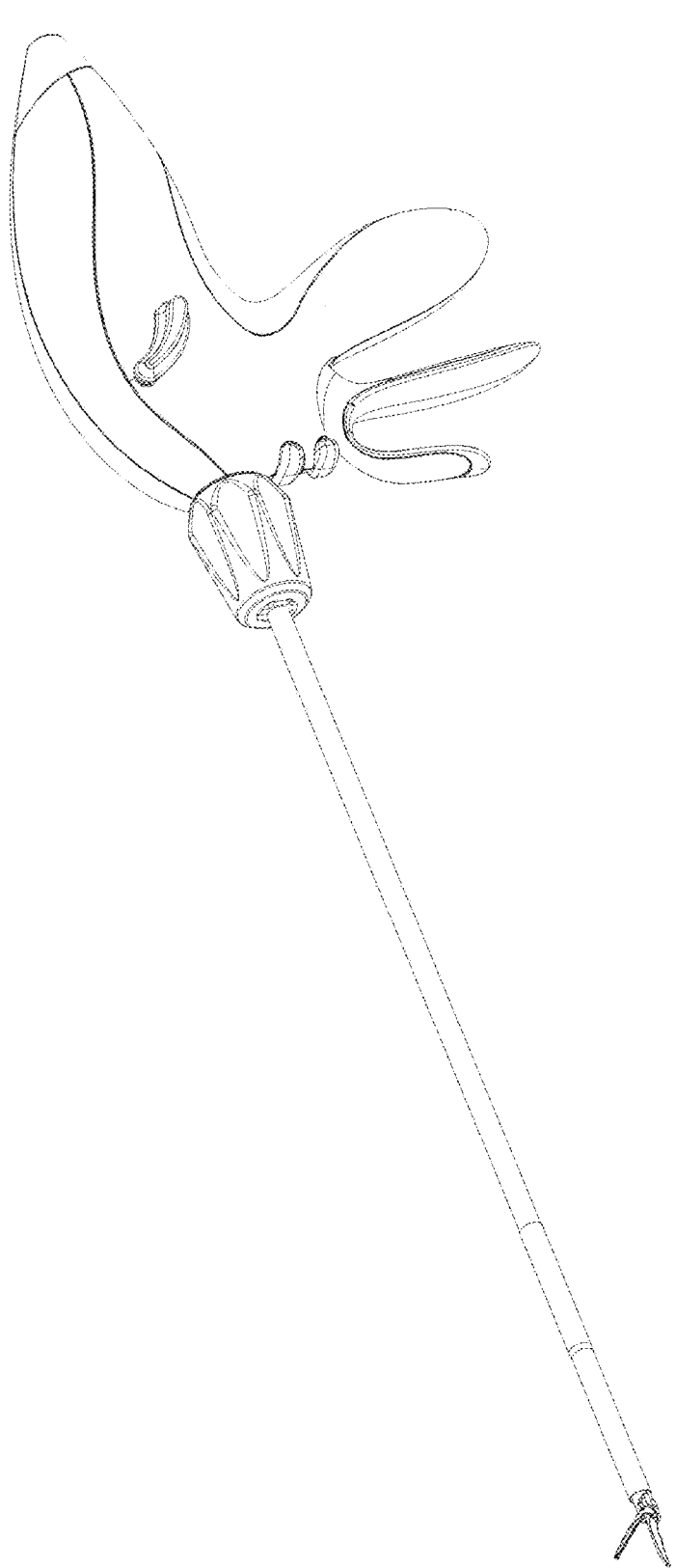
FIG. 1 is a schematic perspective view illustrating a multifunctional surgical instrument according to the present invention.

As shown in FIG. 1, the present invention discloses a multifunctional surgical instrument applied to endoscopic surgery or open surgery.

Figure 2:
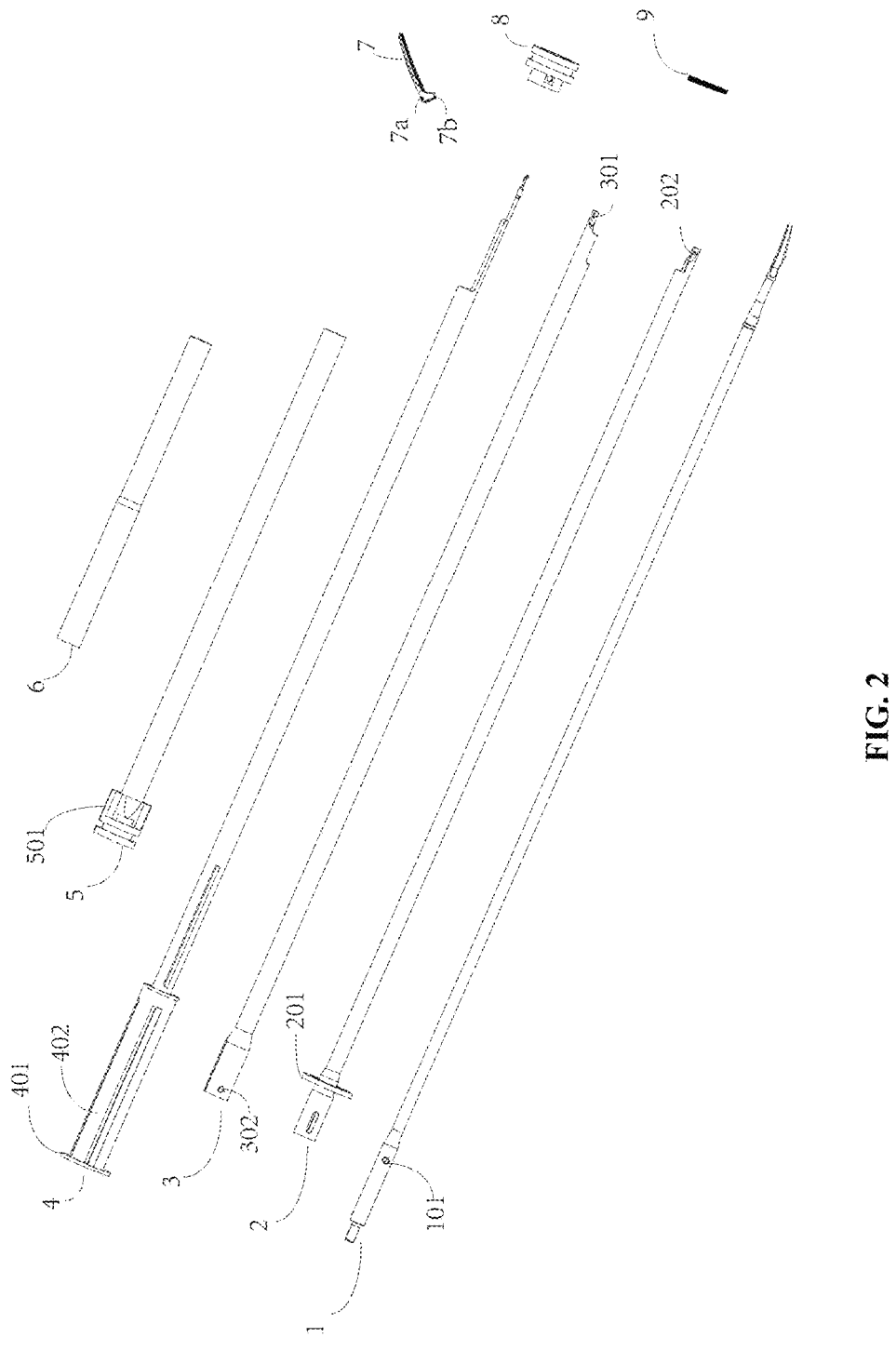
FIG. 2 shows an exploded view of a sleeve assembly of the multifunctional surgical instrument of the present invention.
Figure 3:
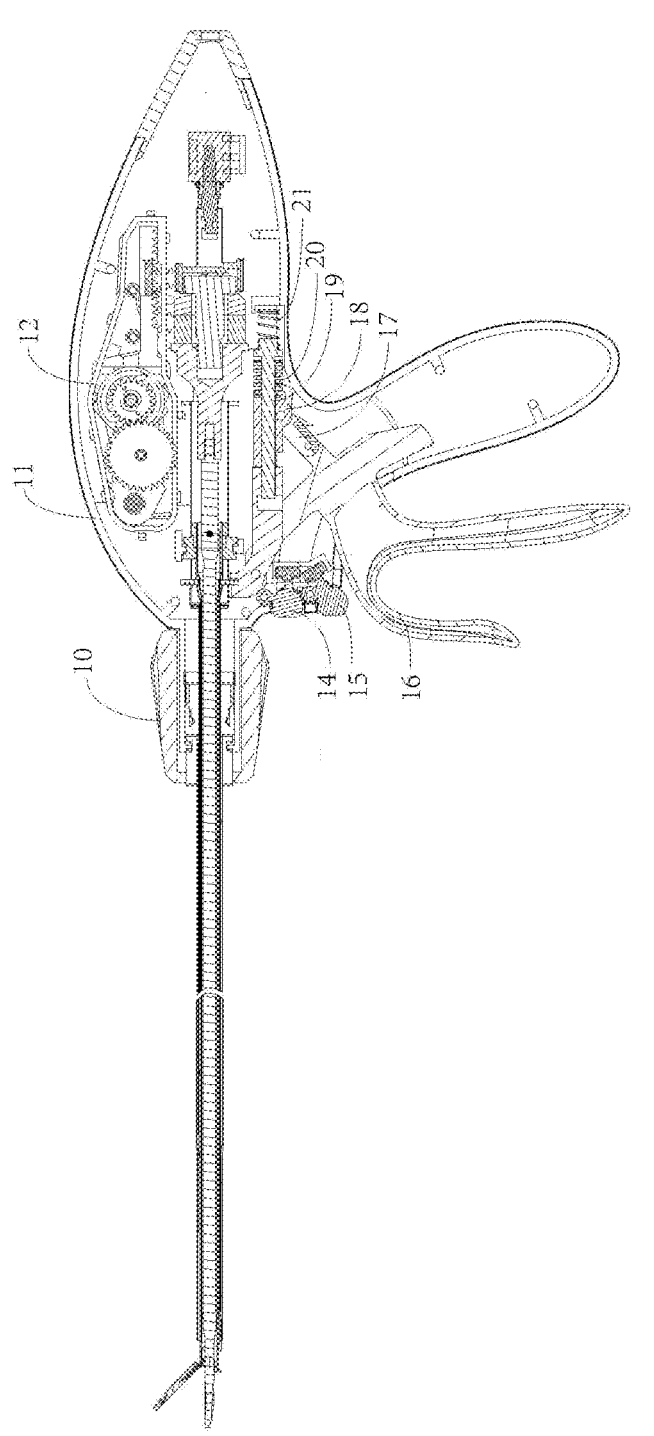
FIG. 3 shows a schematic cross-sectional view of a multifunctional surgical instrument according to the present invention.
Figure 4:
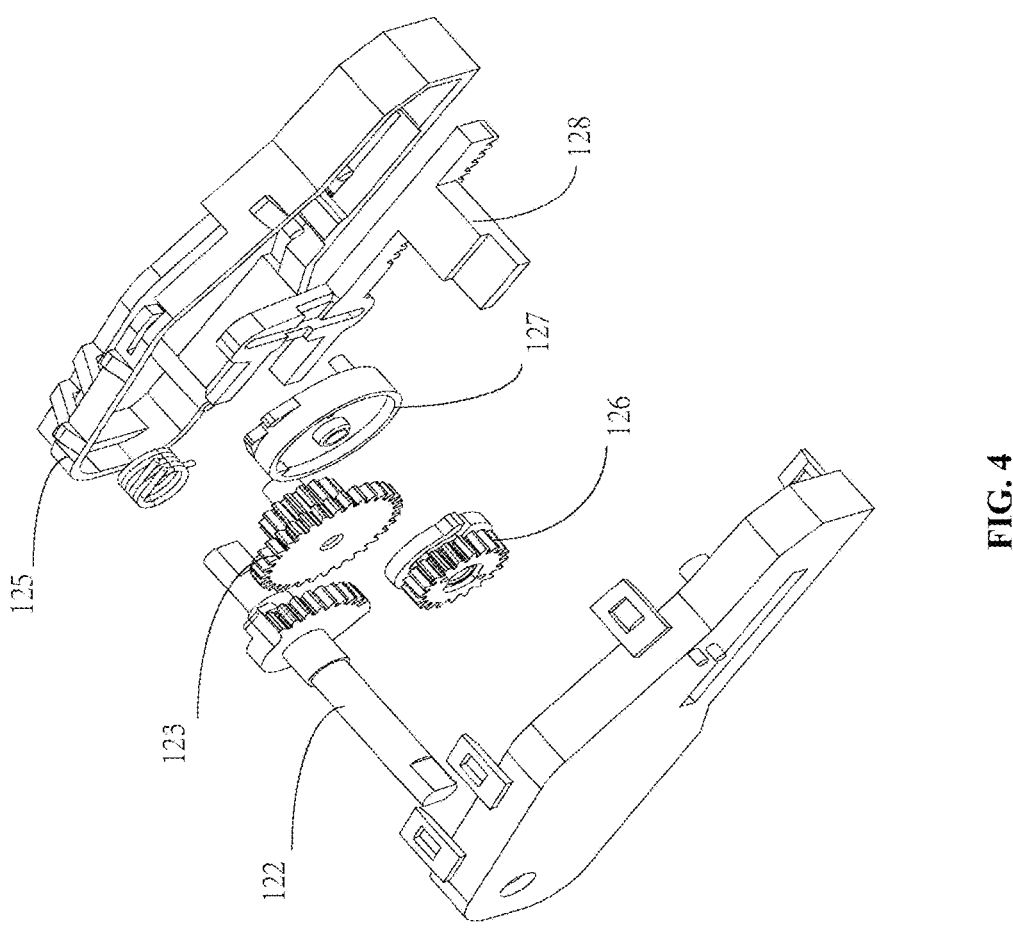
FIG. 4 schematically shows the exploded view of the gearbox of the multifunctional surgical instrument of the present invention.
Figure 5:
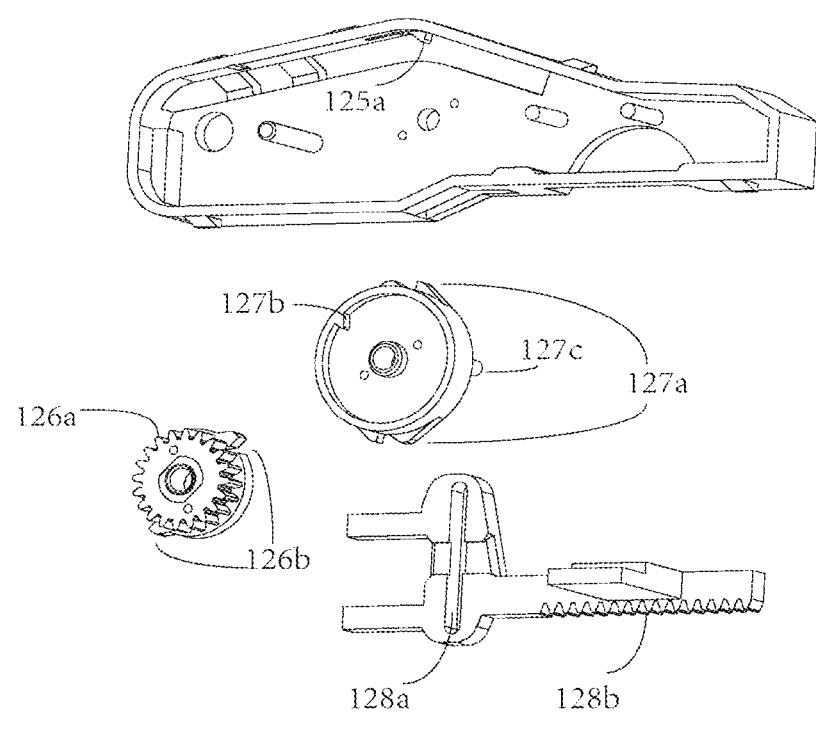
FIG. 5 shows a schematic view of parts of a gearbox of a multifunctional surgical instrument according to the present invention.
Figure 6:
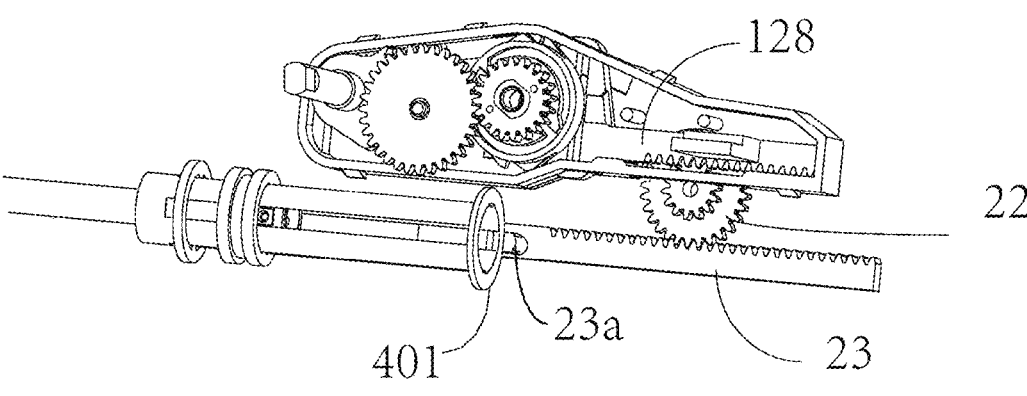
FIG. 6 shows a schematic view of the monopole extension and retraction enabling mechanism of the multifunctional surgical instrument of the present invention.
Figure 7:
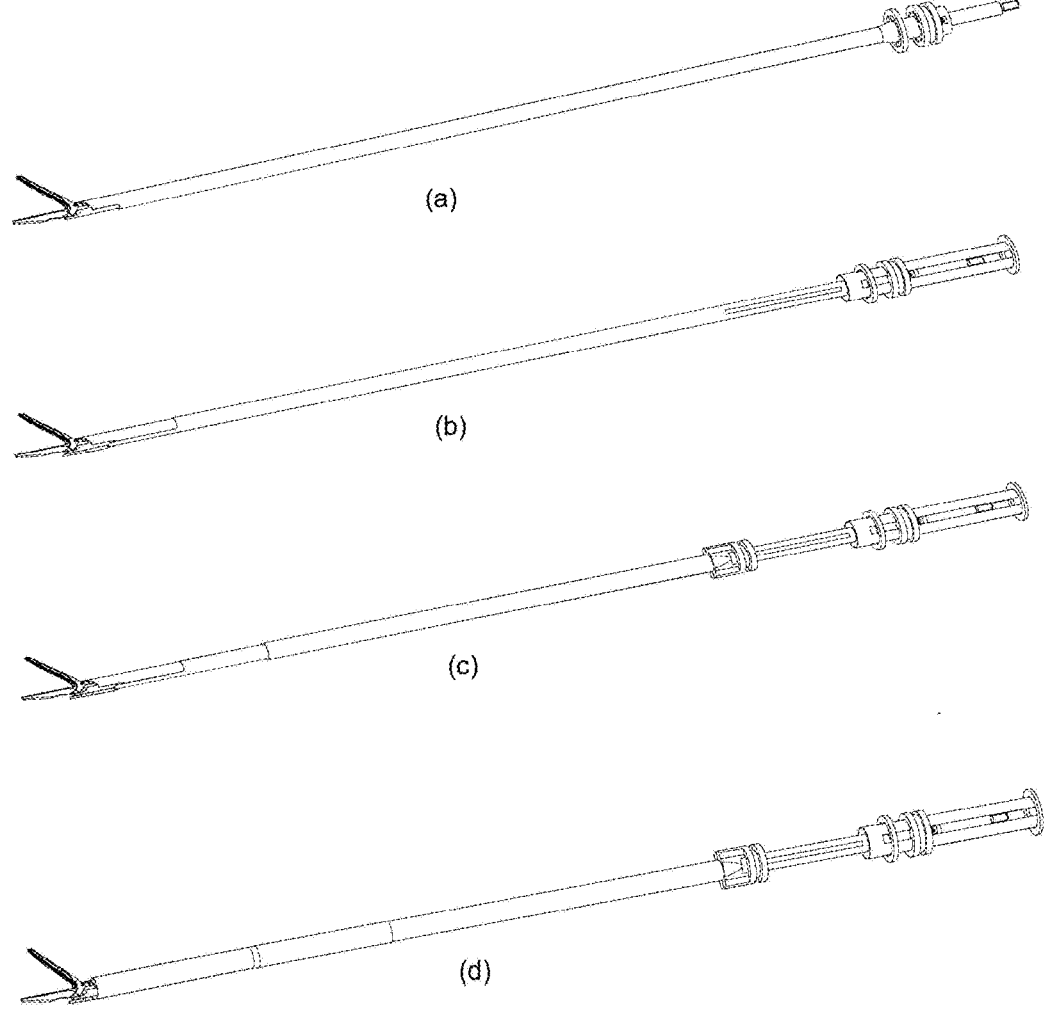
FIG. 7 is a schematic view showing an assembly process of components of the multifunctional surgical instrument sleeve assembly of the present invention.

Referring to FIGS. 2 and 3, the multifunctional surgical instrument according to a preferred embodiment of the present invention comprises a housing 11, a trigger 16 provided on the housing 11, an ultrasonic transducer provided inside the housing 11, and a blade shaft assembly that transmits ultrasonic energy generated by the ultrasonic transducer and electrical energy generated by the system. Specifically, the blade shaft assembly is composed of a multi-layer structure which includes respectively a waveguide 1, a connecting sleeve 2, a support sleeve 3, a monopolar sleeve 4, an outer insulation tube 5 and an outer insulation jacket 6 from inside to outside, and a sleeve holder 8 axially fixed in the housing 11, which can rotate and cannot move axially.

Specifically, the proximal end of the waveguide 1 is fixedly connected to the ultrasonic transducer, and the distal end thereof protrudes outside the housing 11 and forms an ultrasonic blade. The connecting sleeve 2 is sleeved on the circumference of the waveguide 1 and can move axially relative to the waveguide 1. The support sleeve 3 is sleeved on the circumference of the connecting sleeve 2 and is axially fixed with the waveguide 1.

The sleeve holder 8, the waveguide 1 and the support sleeve 3 respectively comprise corresponding pin holes 8*a*, 101 and 302, and the three are axially fixed and can be axially rotated at the same time by means of a penetrating pin 9. The connecting sleeve 2 is provided with an elongated slot 203, and the pin 9 penetrates the elongated slot 203 so that the connecting sleeve 2 can move axially relative to the waveguide 1. Further included is a clamping arm 7 fitted at the distal ends of the connecting sleeve 2 and the support sleeve 3, and the axial movement of the connecting sleeve 2 drives the clamping arm 7 to open and close relative to the waveguide 1. The distal end of the connecting sleeve 2 is provided with a square hole 202, the distal end of the support sleeve 3 is provided with a round hole 301, a round hole 7*a* on the clamping arm 7 is articulated with the round hole 301 at the distal end of the support sleeve 3 via a rotating shaft. A protrusion 7*b* on the clamping arm 7 is clamped into the square hole 202 at the distal end of the connecting sleeve 2.

The trigger 16 generates a first driving force that drives the coupling sleeve 2 to move axially relative to the waveguide 1 via a horizontal yoke 19. The proximal end of the connecting sleeve 2 is flared and opened. A metal circular ring 201 is welded in the flared region. The circular ring 201 is connected to the annular groove 191*a* of the horizontal yoke. The connecting sleeve 2 slides relative to the support sleeve 3 under the pull of the horizontal yoke 19, and drives the protrusion 7*b* of the clamping arm 7 to rotate around the rotating shaft to achieve the opening and closing of the clamping arm 7.

The monopolar sleeve 4 is sleeved on the circumference of the support sleeve 3. The proximal end of the monopolar sleeve 4 has an elongated slot 402 through which the pin 9 penetrating for limiting the sliding stroke of the monopolar sleeve 4.

The outer insulation tube 5 is coated on the outside of the monopolar sleeve 4 and the two are not fixed to each other. The proximal end 501 of the outer insulation tube 5 is connected to the rotating wheel 10 on the housing 11 and rotates with the rotating wheel 10. The outer insulation jacket 6 is coated on the distal end of the monopolar sleeve 4 and is fixed with the monopolar sleeve 4 and moves with the monopolar sleeve 4.

As shown in connection with FIGS. 2 to 6, the monopolar sleeve 4 is moved axially relative to the housing 11 by a second driving force. Preferably, the source of the second driving force is a gearbox 12 provided within the housing 11, which is provided at the proximal end of the monopolar sleeve 4.

A monopole functional unit is welded at the distal end of the monopolar sleeve 4, and the functions thereof comprise one or more of pure cutting, mixed cutting, monopole electrocoagulation and electrocautery. A layer of multi-grooved tube is welded to the proximal end and a circular ring 401 is welded to the proximal end. A recessed structure 23*a* is provided at the distal end of the rack 23 which is coupled to the gearbox 12, and the circular ring 401 is connected to the recessed structure 23*a*, so that the monopolar sleeve 4 performs a reciprocating motion when the rack 23 receives the output of the gearbox 12, thereby achieving the functions of extending and retracting the monopolar sleeve 4.

According to the present invention, the gearbox 12 provides a switching function and comprises:

a reciprocating rotary drive gear 122, and a transmission gear set, comprising a connecting gear 123 and a ratchet 126;

wherein the connecting gear 123 is configured to mesh with the drive gear 122 and enlarge the transmission distance to the ratchet 126;

the ratchet 126 has a double circumference structure which is respectively a gear 126*a* for receiving power and two resilient claws 126*b* symmetrically arranged at 180° on the circumference of the ratchet 126, and the arrangement face of the claws 126*b* is parallel to the gear 126*a* in space;

a reversing idler wheel 127, having a single tooth 127*b* cooperating with the claw 126*b*, two protrusions 127*a* symmetrically provided on the circumference of the reversing idler wheel 127 and cooperating with the limiting mechanism 125*a* of the gear seat 125, the protrusions 127*a* being a ratchet tooth structure, and an eccentric cylinder 127*c* axially provided on one end face of the reversing idler wheel 127; and a rack slider 128, reciprocatingly and slidably provided in the gearbox 12 and having an elongated slot 128*a* provided perpendicular to the reciprocating sliding direction, and a short rack 128*b* provided in correspondence with the reciprocating sliding direction.

The short rack 128b enlarges the transmission distance to the rack 23 through the conversion gear 22.

Referring in detail to FIGS. 4, 5, 6 and 7, the drive gear 122 has a fan-shaped structure, which is moved from a starting position to an extreme position after receiving power (which may be electrically driven or manually driven), and outputs rotation to a gear 126a of a ratchet 126 through a connecting gear 123. One of two claws 126b of the ratchet 126 pushes a single tooth 127b of the reversing idler wheel 127, so that the reversing idler wheel 127 rotates half a cycle. The reversing idler wheel 127 is provided with two protrusions 127a distributed at 180°, and the action process of the reversing idler wheel 107 starts when the protrusion 127a slide out from the limiting mechanism 125a of the gear seat 125, and ends when the protrusion 127a at the other end sliding into the limiting mechanism 125a again. The protrusion 127a and the limiting mechanism 125a form an anti-reverse mechanism for restricting the reverse rotation of the reversing idler wheel 127. The drive gear 122 returns to the starting position from the extreme position, and the ratchet 126 rotates in the reverse direction. Since the protrusion 127a of the reversing idler wheel 127 is caught in the limiting mechanism of the gear seat 125, the driving wheel 127 cannot rotate in the reverse direction, and the ratchet 126 passes over the single tooth 127b, completing the drive gear resetting process. Each time the drive gear 122 completes the process described above, the reversing idler wheel 127 will complete a half-circle rotation.

The eccentric cylinder 127c on the end face of the reversing idler wheel 127 performs a reciprocating motion in the groove 128a of the rack slider 128. Each time the reversing idler wheel 127 completes a half-circle rotation, the eccentric cylinder 127c drives the rack slider 128 to complete a horizontal sliding process from the distal end to the proximal end or from the proximal end to the distal end, thereby achieving the function of reciprocating output of the gearbox 12.

The gearbox 12 amplifies the output of the rack slider 128 to the rack 23 via the conversion gear 22, so that the stroke of the rack 23 reaches the design value.

Figure 8:
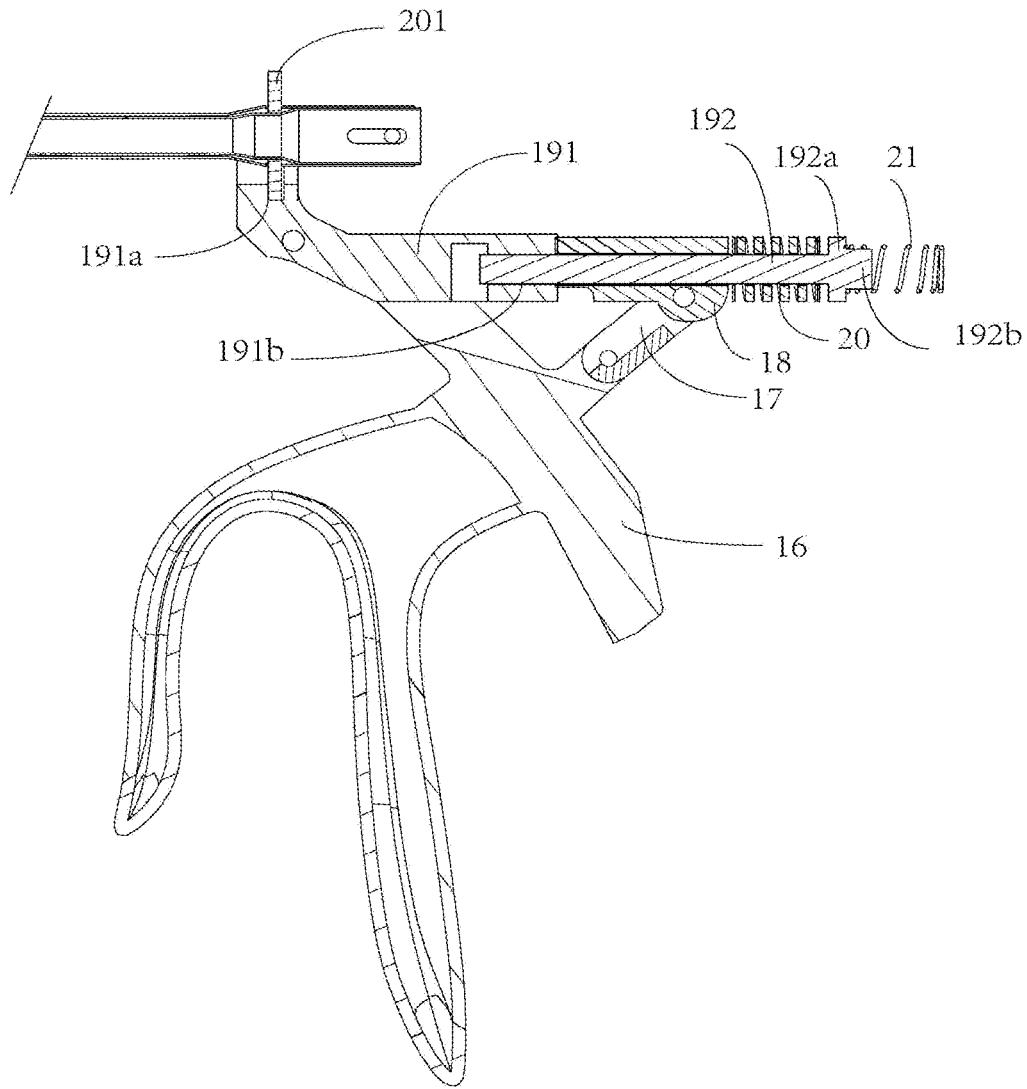
FIG. 8 shows a cross-sectional schematic view of a multifunctional surgical instrument holder drive mechanism of the present invention.
Figure 9:
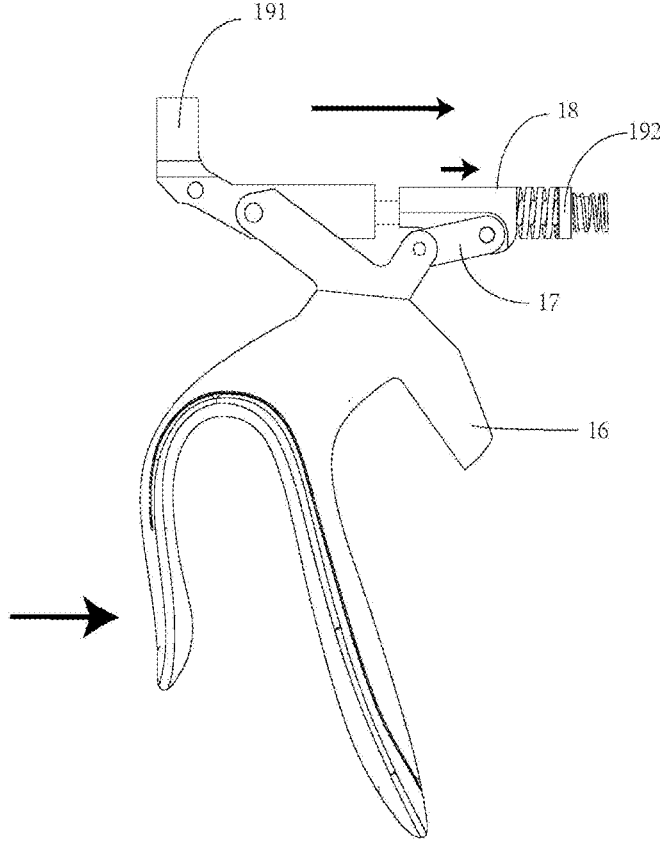
FIG. 9 is a diagram showing the process of applying force to the clamping and driving mechanism of the multifunctional surgical instrument according to the present invention.
Figure 10:
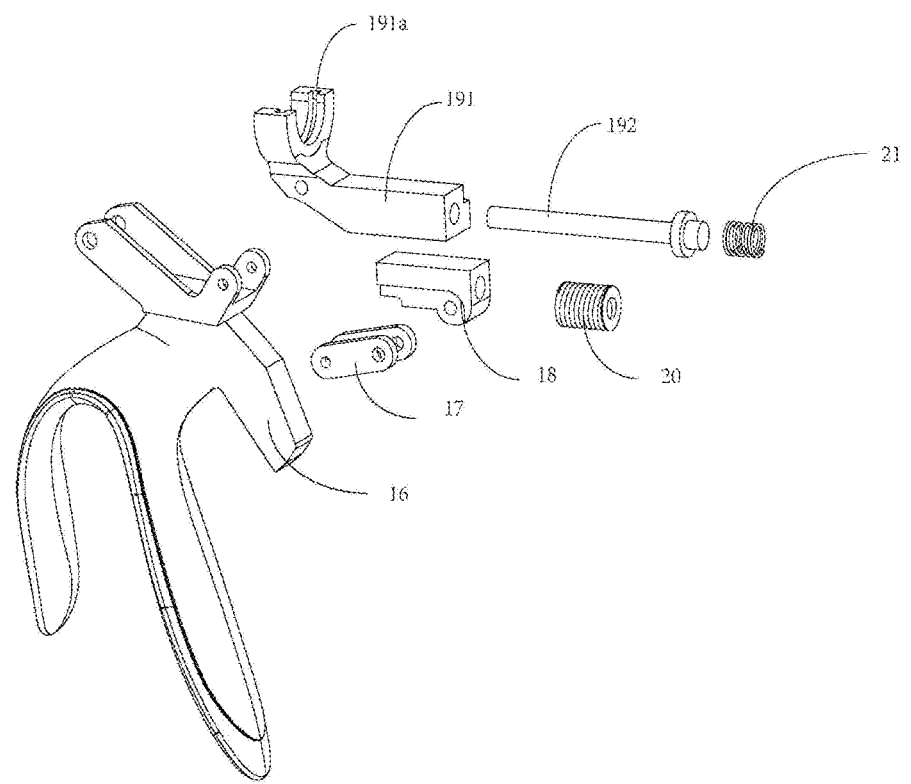
FIG. 10 schematically shows an exploded view of the clamping force driving mechanism of the multifunctional surgical instrument of the present invention.

Referring in detail to FIGS. 8, 9 and 10, the horizontal yoke 19 comprises a distal plastic piece 191 and a proximal metal piece 192 connected to each other by a threaded structure 191b. The proximal metal piece 192 successively penetrates the first spring 20 and the slider 18, and then pre-compresses the first spring 20 and is connected to the distal plastic piece 191. The proximal metal piece 192 has a stop circular ring 192a at its end to provide a reaction force to the first spring 20 when the slider 18 is pressed. The slider 18 is provided with a pin hole to be articulated to one end hole of the connecting rod 17. The other end hole of the connecting rod 17 is articulated with the round hole of the trigger 16.

The distal plastic piece 191 is provided with the annular groove 191a, and the annular groove 191a is connected to a circular ring 201 at the proximal end of the connecting sleeve 2. The circular ring 201 can rotate in the groove 191a and cannot move axially.

The horizontal yoke 19 further comprises a second spring 21 pre-compressed and mounted between a boss 192b on the proximal metal piece 192 and the housing 11 for providing a restoring force to the horizontal yoke 19 to open the clamping arm 7.

The trigger 16 is provided with a rotating shaft hole to be articulated to the housing 11, so that the function of the trigger 16 rotating around a shaft is achieved. As shown in FIG. 9, the trigger 16 rotates in the direction of the arrow, and pushes the slider 18 to move in the direction of the arrow via the connecting rod 17. When the horizontal yoke 19 pulls the connecting sleeve 2 to move until the clamping arm 7 is clamped, the slider 18 gradually compresses the first spring 20, applies elastic force to the horizontal yoke 19, and then outputs force to the clamping arm 7 through the connecting sleeve 2.

Figure 11:
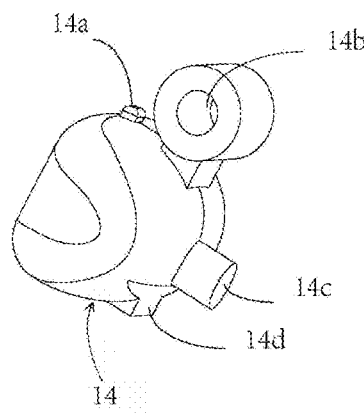
FIG. 11 shows a schematic view of a multifunctional surgical instrument trigger switch of the present invention.
Figure 11:
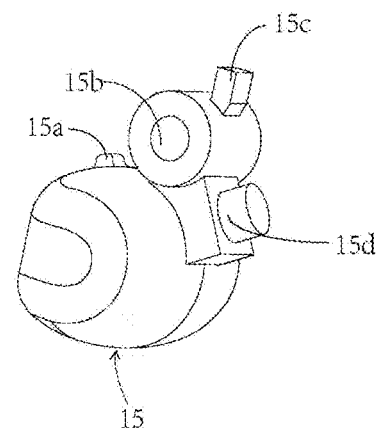
Figure 11:
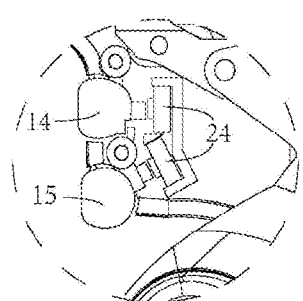
Figure 12:
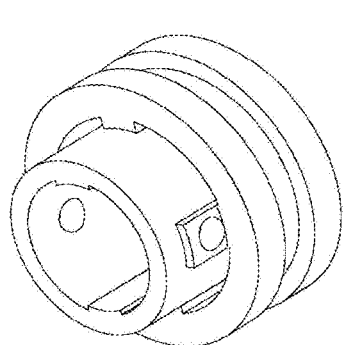
FIG. 12 shows a schematic view of a multifunctional surgical instrument sleeve holder of the present invention.
Figure 12:
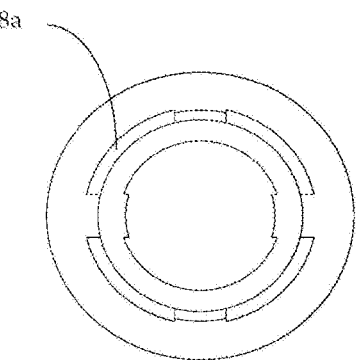

As shown in connection with FIGS. 3, 11 and 12, a first trigger switch 14 and a second trigger switch 15 are provided on the trigger 16, and a simultaneous trigger preventing structure is provided there between. The first trigger switch 14 and the second trigger switch 15 rotate about their rotating shafts 14b and 15b, respectively, which are fixed to the housing 11. When the first trigger switch 14 is triggered, an upper contact 14c thereof triggers the micro-switch 24. The step 14d is in contact with the protruding structure 15c of the second trigger switch 15, so that the second trigger switch 15 cannot be pressed downward, and the function of preventing simultaneous triggering is achieved. Similarly, when the second trigger switch 15 is triggered, the upper contact 15d thereof triggers the micro-switch 24. The protrusion structure 15c is in contact with the step 14d of the first trigger switch 14, so that the first trigger switch 14 cannot be pressed downward, and the function of prevent simultaneous triggering is achieved. This ensures that the multifunctional surgical instrument of the present invention outputs only one function during use.

In the preferred embodiment, both the first trigger switch 14 and the second trigger switch 15 are provided with elastic protrusions 14a and 15a, the function of which is to control the wobble of the switch.

The present invention comprises a waveguide 1 and a monopolar sleeve 4 which can move relative to each other. When an ultrasonic blade of the waveguide 1 is located at the most distal end, ultrasonic energy is generated to achieve the function of cutting and hemostasis. When the monopolar sleeve 4 is located at the most distal end, high-frequency electric energy is generated to achieve the function of a monopole high-frequency electrotome. The present invention integrates two functions of a surgical scalpel to simplify the process of frequently changing surgical knives in an operating room, which may facilitate use by a surgeon. The present invention also has a simultaneous trigger preventing structure for effectively prevents simultaneous triggering of the switch.

The above is only a preferred embodiment of the present invention, and it should be noted that the above-mentioned preferred embodiment should not be construed as limiting the present invention. The scope of the present invention should be determined by the scope of the appended claims. It will be apparent to a person skilled in the art that various modifications and variations can be made in the present invention without departing from the spirit or scope of the disclosure.

What is claimed is:

1. A multifunctional surgical instrument, comprising a housing, a trigger provided on the housing, an ultrasonic transducer provided inside the housing, and a blade shaft assembly that transmits ultrasonic energy from the ultrasonic transducer and electrical energy generated by a system, wherein the blade shaft assembly comprises:

a waveguide, with a proximal end thereof being fixedly connected to the ultrasonic transducer, and a distal end thereof extending out of the housing and forming an ultrasonic blade;

a connecting sleeve sleeved on the circumference of the waveguide and axially movable with respect to the waveguide;

a support sleeve sleeved on the circumference of the connecting sleeve and axially fixed with respect to the waveguide;

a clamping arm fitted at distal ends of the connecting sleeve and the support sleeve, and the axial movement of the connecting sleeve drives the clamping arm to open and close relative to the waveguide;

a monopolar sleeve sleeved on the circumference of the support sleeve;

a gearbox provided within the housing, configured to be located at a proximal end of the monopolar sleeve, and drive the monopolar sleeve to move axially relative to the housing; and a sleeve holder axially fixed in the housing, wherein the waveguide and the support sleeve are axially fixed to the sleeve holder and able to rotate axially at the same time.

2. The multifunctional surgical instrument according to claim 1, wherein the sleeve holder, the waveguide and the support sleeve comprises corresponding pin holes respectively; and the sleeve holder, the waveguide and the support sleeve are axially fixed by a penetrating pin, wherein the connecting sleeve is provided with an elongated slot, and the pin penetrates the elongated slot so that the connecting sleeve moves axially relative to the waveguide.

3. The multifunctional surgical instrument according to claim 2, wherein the proximal end of the monopolar sleeve has an elongated slot through which the pin penetrates to limit the stroke of the monopolar sleeve.

4. The multifunctional surgical instrument according to claim 3, wherein the monopolar sleeve has a circular ring at the proximal end, and a recessed structure is provided at a distal end of a rack coupled to the gearbox, the circular ring is coupled to the recessed structure so that the monopolar sleeve performs a reciprocating motion when the rack receives output of the gearbox.

5. The multifunctional surgical instrument according to claim 4, wherein the gearbox comprises:

a reciprocating rotary drive gear;

a transmission gear set, comprising a connecting gear and a ratchet, wherein the connecting gear is configured to engage the drive gear and enlarge a transmission distance to the ratchet; the ratchet has a gear meshing with the connecting gear and two claws provided symmetrically on the circumference of the ratchet;

a reversing idler wheel, having a single tooth cooperating with the claw, two protrusions symmetrically provided on the circumference of the reversing idler wheel and cooperating with a limiting mechanism of a gear seat, and an eccentric cylinder axially provided on one end face of the reversing idler wheel; and a rack slider, reciprocatingly and slidably provided in the gearbox and having an elongated slot provided perpendicular to the reciprocating sliding direction, and a short rack provided in correspondence with the reciprocating sliding direction.

6. The multifunctional surgical instrument according to claim 5, wherein the short rack enlarges the transmission distance to the rack by means of a conversion gear.

7. The multifunctional surgical instrument according to claim 1, wherein a distal end of the connecting sleeve is provided with a square hole, a distal end of the support sleeve is provided with a round hole, a round hole on the clamping arm and the round hole on the distal end of the support sleeve are articulated via a rotating shaft, and a protrusion on the clamping arm is snapped into the square hole on the distal end of the connecting sleeve.

8. The multifunctional surgical instrument according to claim 7, wherein the trigger generates a first driving force to drive the connecting sleeve to move axially relative to the waveguide via a horizontal yoke, a circular ring at the proximal end of the connecting sleeve is connected to an annular groove of the horizontal yoke, and the connecting sleeve slides relative to the support sleeve under the pull of the horizontal yoke, and drives the protrusion of the clamping arm to rotate around a rotating shaft to realize the opening and closing of the clamping arm.

9. The multifunctional surgical instrument according to claim 8, wherein the horizontal yoke comprises a distal plastic piece and a proximal metal piece which are connected to each other, and the proximal metal piece successively penetrates a first spring and the slider and then pre-compresses the first spring and then is connected to the distal plastic piece; the slider is articulated to the trigger, the distal plastic piece is provided with an annular groove; and further comprises a second spring pre-compressed and mounted between a boss on the proximal metal piece and the housing for providing a restoring force to the horizontal yoke.

10. The multifunctional surgical instrument according to claim 1, wherein the blade shaft assembly further comprises an outer insulation tube and an outer insulation jacket, wherein the outer insulation tube is coated on the outside of the monopolar sleeve, and the outer insulation tube and the monopolar sleeve are not fixed to each other, the proximal end of the outer insulation tube is connected to and rotates with a rotating wheel on the housing, and the outer insulation jacket is coated on the distal end of the monopolar sleeve and is fixed with the monopolar sleeve and moves therewith.

11. The multifunctional surgical instrument according to claim 1, wherein the trigger is provided with a first trigger switch and a second trigger switch having a simultaneous trigger preventing structure therebetween.

12. A multifunctional surgical instrument, comprising a housing, a trigger provided on the housing, an ultrasonic transducer provided within the housing, and a blade shaft assembly that transmits ultrasonic energy from the ultrasonic transducer and electrical energy generated by a system, wherein the blade shaft assembly comprises:

a waveguide, with a proximal end thereof being fixedly connected to the ultrasonic transducer, and a distal end thereof extending out of the housing and forming an ultrasonic blade;

a clamping arm, opened and closed relative to the waveguide by a first driving force; and a monopolar sleeve, sleeved on an outer side of the waveguide and axially moving relative to the housing under action of a second driving force.

13. The multifunctional surgical instrument according to claim 12, wherein a source of the second driving force is a gearbox provided in the housing and provided at the proximal end of the monopolar sleeve, wherein the monopolar sleeve has a circular ring at a proximal end, and a rack coupled to the gearbox has a recessed structure at a distal end, and the circular ring is connected to the recessed structure so that the monopolar sleeve performs a reciprocating motion when the rack receives output of the gearbox.

14. The multifunctional surgical instrument according to claim 13, wherein the gearbox comprises:

a power source that outputs forward and reverse recipro-
cating rotary power;

a ratchet for receiving forward and reverse reciprocating
rotary power, the ratchet having a double circumfer-
ence structure, respectively being a gear for receiving
the power and two resilient claws symmetrically
arranged at 180° on the circumference of the ratchet,
the arrangement face of the claws being parallel to the
gear in space;

a rack slider reciprocatingly and slidably provided in the
gearbox; and a reversing idler wheel for converting the forward and
reverse reciprocating rotary power of the ratchet into an
axial reciprocating motion of the rack slider.

15. The multifunctional surgical instrument according to
claim 14, wherein an inside of the reversing idler wheel
comprises a single tooth cooperating with the claw.

16. The multifunctional surgical instrument according to
claim 15, wherein the reversing idler wheel further has an
anti-reversing mechanism comprising two protrusions sym-
metrically provided at 180° on the circumference of the
reversing idler wheel and cooperating with a limiting
mechanism of a gear seat, wherein the protrusions are of a
ratchet tooth structure to restrict the reverse rotation of the
reversing idler wheel; and wherein the reversing idler wheel further comprises an
eccentric cylinder provided axially on one end surface
thereof, the rack slider has an elongated slot provided
perpendicular to the reciprocating sliding direction, and
the eccentric cylinder is inserted into the elongated slot.

17. A multifunctional surgical instrument according to
claim 12, further comprising a sleeve holder axially fixed in
the housing, wherein the waveguide is axially fixed to the
sleeve holder and axially rotatable at the same time.

18. The multifunctional surgical instrument according to
claim 12, wherein the blade shaft assembly further com-
prises:

a connecting sleeve sleeved on the circumference of the
waveguide and axially movable with respect to the
waveguide; and a support sleeve sleeved on the circumference of the
connecting sleeve and axially fixed on the sleeve holder
together with the waveguide;

wherein the clamping arm is fitted at distal ends of the
connecting sleeve and the support sleeve, the trigger
generates a first driving force to drive the connecting
sleeve to move axially relative to the waveguide via a
horizontal yoke, a circular ring at the proximal end of
the connecting sleeve is connected to an annular groove
of the horizontal yoke, the connecting sleeve slides
relative to the support sleeve under the pull of the
horizontal yoke, and drives a protrusion of the clamp-
ing arm to rotate around a rotating shaft to achieve
opening and closing of the clamping arm.

19. A multifunctional surgical instrument, comprising a
housing, a trigger provided on the housing, and a blade shaft
assembly, wherein the blade shaft assembly is configured to
selectively receive and transmit ultrasonic energy provided
by an ultrasonic transducer through a switching mechanism
located within the housing for cutting and hemostasis, or
selectively transmit high-frequency electrical energy to
achieve a function of a monopole high-frequency electro-
tome, wherein the blade shaft assembly comprises:

a waveguide configured to transmit ultrasonic energy
generated by the transducer; and a monopolar sleeve movable relative to the waveguide;
wherein when an ultrasonic blade of the waveguide is
located at the most distal end, ultrasonic energy is
generated to perform cutting and hemostasis; and when
the monopolar sleeve is located at the most distal end,
high-frequency electric energy is transmitted to achieve
the function of the monopole high-frequency electro-
tome.

20. The multifunctional surgical instrument according to
claim 19, wherein the ultrasonic transducer is provided
within the housing or external to and attached to the blade
shaft assembly.

21. The multifunctional surgical instrument according to
claim 19, wherein the blade shaft assembly further com-
prises:

a connecting sleeve sleeved on the circumference of the
waveguide and axially movable with respect to the
waveguide;

a support sleeve sleeved on the circumference of the
connecting sleeve and axially fixed with the wave-
guide;

a clamping arm fitted at distal ends of the connecting
sleeve and the support sleeve, and the axial movement
of the connecting sleeve drives the clamping arm to
open and close relative to the waveguide; and a sleeve holder axially fixed in the housing, wherein the
waveguide and the support sleeve are axially fixed to
the sleeve holder and can rotate axially at the same
time.

22. The multifunctional surgical instrument according to
claim 21, wherein the blade shaft assembly further com-
prises an outer insulation tube and an outer insulation jacket,
wherein the outer insulation tube is coated on the outside of
the monopolar sleeve, and the outer insulation tube and the
monopolar sleeve are not fixed to each other, and a proximal
end of the outer insulation tube is connected to a rotating
wheel on the housing and rotates with the rotating wheel,
and the outer insulation jacket is coated on a distal end of the
monopolar sleeve and is fixed with the monopolar sleeve
and moves therewith.

23. The multifunctional surgical instrument according to
claim 21, wherein the switching mechanism is a gearbox, the
monopolar sleeve is driven by the gearbox to move axially
relative to the ultrasound guide rod, and the gearbox com-
prises:

a reciprocating rotary drive gear;

a transmission gear set, comprising a connecting gear and
a ratchet, the connecting gear is configured to engage
the drive gear and enlarge a transmission distance to the
ratchet; the ratchet has a gear meshing with the con-
necting gear and two claws provided symmetrically on
the circumference of the ratchet;

a reversing idler wheel, having a single tooth cooperating
with the claw, two protrusions symmetrically provided
on the circumference of the reversing idler wheel and
cooperating with a limiting mechanism of a gear seat,
and an eccentric cylinder axially provided on one end
face of the reversing idler wheel; and a rack slider reciprocatingly and slidably provided in the
gearbox and having an elongated slot provided perpen-
dicular to the reciprocating sliding direction, and a
short rack provided in correspondence with the recip-
rocating sliding direction.

24. The multifunctional surgical instrument according to
claim 21, wherein the trigger is provided with a first trigger switch and a second trigger switch having a simultaneous trigger preventing structure therebetween.

* * * * *